United States Patent

Rogers et al.

[11] Patent Number: 6,159,010
[45] Date of Patent: Dec. 12, 2000

[54] FENESTRATED DENTAL COPING

[75] Inventors: Dan Paul Rogers, Royal Palm Beach; Stephan S. Porter, Palm Beach Gardens, both of Fla.

[73] Assignee: Implant Innovations, Inc., Palm Beach Gardens, Fla.

[21] Appl. No.: 09/295,262

[22] Filed: Apr. 20, 1999

Related U.S. Application Data

[60] Provisional application No. 60/082,842, Apr. 23, 1998.

[51] Int. Cl.[7] .............................. A61C 13/12; A61C 8/00
[52] U.S. Cl. ......................................... 433/172; 433/201.1
[58] Field of Search ................................ 433/191, 201.1, 433/202.1, 173, 172

[56] References Cited

U.S. PATENT DOCUMENTS

| | | | |
|---|---|---|---|
| 4,575,340 | 3/1986 | Lustig | 433/173 |
| 4,722,688 | 2/1988 | Lonca | 433/173 |
| 4,746,293 | 5/1988 | Lundgren et al. | 433/173 |
| 4,790,753 | 12/1988 | Fradera | 433/174 |
| 4,850,870 | 7/1989 | Lazzara et al. | 433/174 |
| 4,850,873 | 7/1989 | Lazzara et al. | 433/220 |
| 4,915,629 | 4/1990 | Sellers | 433/173 |
| 5,104,318 | 4/1992 | Piche et al. | 433/174 |
| 5,110,292 | 5/1992 | Balfour et al. | 433/173 |
| 5,133,662 | 7/1992 | Metcalfe | 433/173 |
| 5,259,759 | 11/1993 | Jörnéus et al. | 433/173 |
| 5,458,488 | 10/1995 | Chalifoux | 433/173 |
| 5,527,182 | 6/1996 | Willoughby | 433/172 |
| 5,667,384 | 9/1997 | Sutter et al. | 433/172 |
| 5,681,167 | 10/1997 | Lazarof | 433/174 |
| 5,688,123 | 11/1997 | Meiers et al. | 433/173 |
| 5,752,828 | 5/1998 | Andersson et al. | 433/172 |

FOREIGN PATENT DOCUMENTS

| | | |
|---|---|---|
| 0 629 384 A1 | 12/1994 | European Pat. Off. . |
| 40 28 855 A1 | 3/1992 | Germany . |
| 1 291 470 | 10/1972 | United Kingdom . |
| WO 97/14371 A1 | 4/1997 | WIPO . |
| WO 97/28755 A1 | 8/1997 | WIPO . |

*Primary Examiner*—Todd E. Manahan
*Attorney, Agent, or Firm*—Jenkens & Gilchrist

[57] ABSTRACT

A dental coping is set forth for placement over an abutment post that is attached to and protruding above a dental implant. The abutment post includes an outer surface with at least one structure for non-rotationally engaging a prosthetic tooth. The coping includes a base portion having an internally tapered surface for mating with a support surface of the implant. A wall extends away from the base portion for enveloping the abutment post. The wall includes at least one aperture for being aligned with and providing access to at least one of the non-rotational attachment engagement structures of the abutment post. The apertures are especially useful in the process of making the prosthetic tooth by allowing wax material to pass therethrough and engage the non-rotational features of an analog device replicating the abutment post such that a castable material will form antirotational features for mating with the antirotational features of the abutment post.

34 Claims, 1 Drawing Sheet

6,159,010

FENESTRATED DENTAL COPING

CROSS REFERENCE TO RELATED APPLICATION

This is a complete application claiming the benefit of copending provisional application Serial No. 60/082,842, filed Apr. 23, 1998.

FIELD OF THE INVENTION

This invention relates general to dental components and, in particular, to a dental coping that includes a plurality of apertures along its side surface and is for supporting an artificial tooth on an underlying abutment.

BACKGROUND OF THE INVENTION

This invention relates in general to artificial dental prostheses, more particularly to prostheses retained on a supporting post or posts with a cement (i.e. a cement-retained prostheses) or otherwise. The supporting post may be an endodontic post supported in the patient's natural root or it may be an abutment fixed in an artificial root, commonly called a "dental implant," implanted at an edentulous site in the patient's jawbone. The invention is herein described and illustrated in the latter environment wherein an artificial tooth is fixed on an abutment which in turn is fixed to the dental implant.

Cement-retained prostheses are formed to enclose the supporting post or abutment and to fit tightly at the margin with the implant or natural root. In the illustrated case employing dental implants, the margin is a prefabricated surface of the implant or of a distancing member supported on the implant. This prefabricated surface can be made with engineering precision, and it is desired that the prosthesis (i.e. artificial tooth) be made with equal precision in order to provide a uniformly tight margin that will exclude oral fluids and provide long-term hygienic conditions at the margin. At the same time, the dental abutments that are used with dental implants frequently are fitted with antirotational holding structures, such as a flat surface(s) or a groove(s), to engage a prosthesis against rotation around the abutment, which is particularly useful when a single tooth is being restored. The present invention enhances the opportunity of restorative dentists and dental laboratories to achieve an ideal margin by removing the inaccuracies that may sometimes be encountered during the impression-making process within the patient's mouth at the margin. Further, the inventive coping can be used to provide accurate anti-rotational structures on the artificial tooth that are to engage the corresponding antirotational structures of the supporting abutment post.

SUMMARY OF THE INVENTION

In accordance with the invention, a coping of generally tubular form is incorporated in the artificial tooth, using any one of known processes. This coping is shaped to enclose the abutment at least at its base portion where it attaches to the dental implant. The coping has at its base a margin-forming section which can be shaped to meet uniformly and precisely with the dental implant. The remainder of the coping which extends supragingivally from the base is fenestrated with apertures that are located to expose the antirotational grooves or flats of the abutment.

When the artificial tooth is formed using the coping of the invention via a lost-wax process, the apertures of the coping are aligned with the anti-rotational features of a analog device replicating the abutment. A core for the artificial tooth produced from this method will have projections that extend into the apertures of the coping such that the artificial tooth is free to interlock with the grooves or flats on the abutment while at the same time making use of the improved margin properties of the coping.

This coping can be used in permanent form (e.g. gold) such that it becomes incorporated into, and made integral with, the castable core material of the artificial tooth. Or, it can be made of a burn-out material so that its form and shape are replicated in the artificial tooth by the castable material (e.g. gold) that is replacing, or burning-out, the plastic coping and the adjacent wax.

DETAILED DESCRIPTION OF THE DRAWINGS

Figure 1:
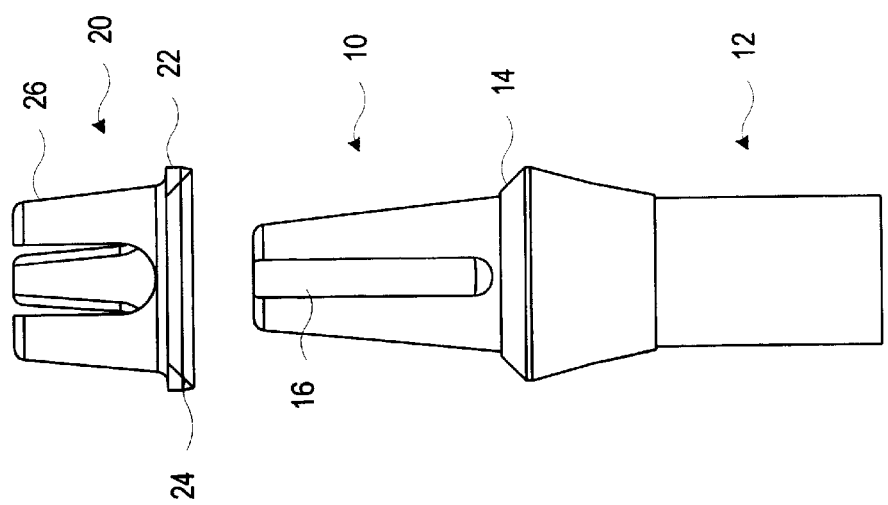
FIG. 1 is an exploded side elevation of a coping of the invention and an assembly of an abutment and a dental implant.

In FIG. 1 a post or abutment 10 ("abutment post") is shown assembled to a dental implant 12. The top surface 14 of the implant 12 is intended to provide marginal support to an artificial tooth (not shown). The abutment post 10 is provided with longitudinally-extending grooves 16 for engaging an artificial tooth against rotation around the post when the artificial tooth is supported on the abutment post 10. The artificial tooth may be cement-retained on the abutment post 10, as is a common practice, or it may be mechanically-retained if desired. These options are well-known, and not part of the invention.

A coping 20 according to the invention has an annularly-shaped base portion 22 with an internally tapered surface 24 for forming a uniform tight margin with the top surface 14 of the implant. The top surface 14 is at approximately a 45° angle with respect to the central axis of the implant 12. Extending supragingivally from the base portion 22, the coping 20 has walls 26 shaped to envelop the abutment post 10 at least at and near the lower portion of the abutment post 10 which meets the implant 12. The walls 26 are preferably tapered inwardly in a direction away from the base portion 22 so as to follow the general contour of the abutment post 10.

Figure 2:
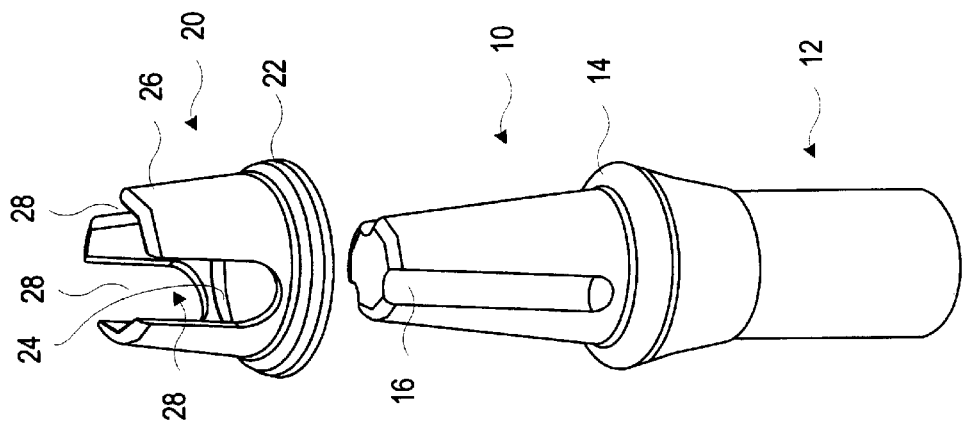
FIG. 2 is an isometric view of the components shown in FIG. 1.
Figure 3:
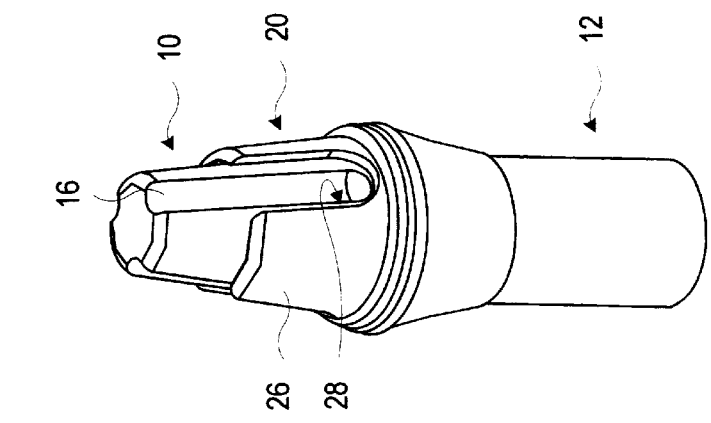
FIG. 3 is an isometric view of the same components shown in FIG. 1 after being assembled.

The walls 26 are fenestrated with apertures 28 that are positioned between adjacent walls 26. The apertures 28 are registered over the grooves 16 so that the grooves 16 in the abutment post 10 are exposed when resting on the abutment post 10. These apertures 28 achieve their functionality during the process by which the artificial tooth is made. When a wax-up of an artificial tooth is formed on an analog device representing the abutment post 10 and the implant 12, the wax will enter through the apertures 28 and engage the grooves of the analog device which replicate the grooves 16 of the abutment post 10. The wax-up is then encapsulated in cement-like material and castable material, such as gold, is poured into an opening in the cement thereby burning-out the wax and leaving a gold core in the shape of the wax. Accordingly, this gold core is attached to and made integral with the coping 20. In this way, an artificial tooth of porcelain, for example, formed on the integral gold core and coping 20 achieves the benefits of a precise margin due to the internally tapered surface 24 of the coping 20 and of an antirotational feature resulting from the castable material formed through the apertures 28 that capable of engaging the grooves 16 of the abutment post 10, as is illustrated in FIG. 3.

The apertures 28 are shown as open at the supragingival end of the coping 20, but fenestration can be provided with apertures of other forms if desired. The aperture 28 may extend for only a portion of the length of walls 26 such that the walls 26 are joined at their upper ends just as they are attached at their lower ends at the base portion 22. Additionally, while only three apertures 28 are shown, the coping 20 could have one or two apertures for engaging the anti-rotational grooves 28 of the abutment post 10. Likewise, more apertures 28 could be added. Preferably, the apertures 28 are at least as wide as or slightly larger than the width of the grooves 28.

While the coping 20 has been described as a metallic piece, it can also be made of a plastic such as acrylic. In this way, the coping 20 can be made to hold an artificial temporary tooth made of common dental plastics, such as acrylic. Thus, the clinician would fit this coping 20 over the abutment post 10 with the apertures 28 aligned with the grooves 28 and apply the acrylic material in the shape of an artificial tooth. The coping 20 and applied acrylic would then be attached to the abutment post 10 with temporary cement. Further the plastic coping 20 can be used to develop a permanent tooth via the lost wax process described above. Here, the molten gold would replace the wax-up and the plastic coping 20 such that the shape of the plastic coping 20, especially its base portion 22 and its tapered internal surface 24, would be reproduced by the resulting gold core as opposed to the metallic coping 20 as described previously.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A dental coping for use with an abutment post that is attached to and protruding above a dental implant, said abutment post including an outer surface with at least one antirotational structure for resisting rotation of a prosthetic tooth mounted thereon, said dental coping comprising:

a base portion having an internal surface for mating with a support surface of said implant;

a wall extending away from said base portion and capable of enveloping at least a portion of said abutment post and having a generally smooth inner surface capable of attachment to said abutment post in a slidable, non-threaded fashion; and at least one aperture in said wall capable of alignment with and providing access to said at least one of said antirotational structures of said abutment post.

2. The dental coping of claim 1, wherein said wall includes a plurality of apertures capable of alignment with and providing access to a plurality of said antirotational structures of said abutment post.

3. The dental coping of claim 1, wherein said wall terminates at an upper end of said dental coping opposing said base portion, said upper end being opened.

4. The dental coping of claim 1, wherein said wall tapers inwardly in a direction away from said base portion.

5. The dental coping of claim 1, wherein said aperture extends entirely along a length of said wall.

6. The dental coping of claim 1, wherein said base portion is annular in shape.

7. The dental coping of claim 1, wherein said base portion extends outwardly to form a shoulder for engaging said prosthetic tooth.

8. The dental coping of claim 1, wherein said internal surface is tapered to match a tapered surface on said implant.

9. The dental coping of claim 1, wherein said coping receives a castable material that solidifies within said apertures.

10. The dental coping of claim 1, in combination with said abutment post and a castable material made integral with said coping and extending at least partially though said apertures, said castable material for engaging said anti-rotational structure of said abutment post.

11. A dental coping to be made into a core structure of an artificial tooth that is to be placed over an abutment post attached to an implant, said dental coping comprising:

a base portion including a surface for engaging a support surface of said implant;

a wall extending upwardly from said base portion having an internal surface generally following an outer surface of said abutment post; and a plurality of apertures in said wall for providing access of a castable material into an internal region of said dental coping.

12. The dental coping of claim 11, wherein said dental coping is metallic.

13. The dental coping of claim 11, wherein said surface of said base portion is tapered.

14. The dental coping of claim 11, wherein said plurality of apertures are spaced in manner to match the circumferential position of antirotational structures on said abutment post.

15. The dental coping of claim 14, wherein said plurality of apertures are symmetrically arranged around said coping.

16. The dental coping of claim 11, wherein said plurality of apertures are opened at a top end of said wall opposing said base portion.

17. The dental coping of claim 11, wherein said base portion extends outwardly to form a shoulder for engaging material replicating a natural tooth.

18. The dental abutment system for supporting an artificial tooth comprising:

an abutment including a lower region for mating with an dental implant and an upper region for protruding above said implant, said upper region including an antirotational feature on an outer surface thereof; and a generally tubular dental coping to be made into a core structure of an artificial tooth that is to be placed over said abutment, said dental coping including a base portion including a surface for engaging a support surface of said implant and a wall extending upwardly from said base portion, said wall having at least one aperture for providing access to said antirotational feature of said abutment, said coping having an inner surface for receiving cement for attaching said coping to said abutment post.

19. The dental abutment system of claim 18, wherein said dental coping is made of a polymeric material.

20. The dental abutment system of claim 19, wherein said dental coping is capable of receiving a material to form a temporary tooth that is cementable to said abutment.

21. The dental abutment system of claim 19, wherein said polymeric material can be replaced by a metallic material through a lost-wax casting process.

22. The dental abutment system of claim 18, wherein said dental coping is a metallic structure.

23. The dental abutment system of claim 18, wherein said apertures of said dental coping are opened at an upper end of said wall opposing said base portion.

24. The dental abutment system of claim 18, wherein said wall of said dental coping has a first tapered internal surface for following the contour of said outer surface of said abutment and said surface for engaging said implant is tapered at a different angle.

25. The dental abutment system of claim 18, wherein said surface of said dental coping for engaging said implant is annular.

26. The dental abutment system of claim 18, wherein said antirotational feature is a longitudinal groove within said outer surface.

27. The method of producing an artificial tooth to be mounted on an abutment attached to an implant, said abutment including at least one antirotational feature on an outer surface for engaging said artificial tooth, comprising:

placing a metallic coping on an analog device representing said implant and abutment;

aligning an aperture of said coping with an antirotational feature of said analog device replicating said antirotational feature of said abutment;

applying a wax material to portions of said coping and into said aperture so as to define a volume where a core structure of said artificial tooth is desired;

encapsulating said wax material in a cement-type material that includes an opening leading to said wax material;

adding a molten castable metal through said opening to replace said wax material and solidify with said coping to develop said core, said castable material passing at least partially into said aperture; and adding a dental material to said core that replicates a natural tooth.

28. The method of claim 27, wherein said coping includes an annular base surface for mating with a portion of said analog device corresponding to said a support surface of said implant.

29. The method of claim 27, wherein said antirotational feature is a longitudinal groove.

30. The method of claim 27, wherein said dental material for replicating said natural tooth is porcelain.

31. The method of claim 27, wherein said aperture of said dental coping is opened at an upper end of said coping.

32. A dental coping for use with an abutment post that is attached to and protruding above a dental implant, said abutment post including an outer surface with a plurality of antirotational structures for resisting rotation of a prosthetic tooth mounted thereon, said dental coping comprising:

a base portion having an internal surface for mating with a support surface of said implant;

a wall extending away from said base portion and capable of enveloping at least a portion of said abutment post; and a plurality of apertures in said wall capable of alignment with and providing access to said at least one of said antirotational structures of said abutment post.

33. A dental coping for use with an abutment post that is attached to and protruding above a dental implant, said abutment post including an outer surface with at least one antirotational structure for resisting rotation of a prosthetic tooth mounted thereon, said dental coping comprising:

a base portion having an internal surface for mating with a support surface of said implant;

a wall extending away from said base portion and capable of enveloping at least a portion of said abutment post, said wall terminates at an upper end of said dental coping opposing said base portion, said upper end being opened; and at least one aperture in said wall capable of alignment with and providing access to said at least one of said antirotational structures of said abutment post.

34. A dental coping for use with an abutment post that is attached to and protruding above a dental implant, said abutment post including an outer surface with at least one antirotational structure for resisting rotation of a prosthetic tooth mounted thereon, said dental coping comprising:

a base portion having an internal surface for mating with a support surface of said implant;

a wall extending away from said base portion and capable of enveloping at least a portion of said abutment post;

at least one aperture in said wall capable of alignment with and providing access to said at least one of said antirotational structures of said abutment post; and a castable material that solidifies within said at least one aperture.

\* \* \* \* \*

UNITED STATES PATENT AND TRADEMARK OFFICE
CERTIFICATE OF CORRECTION

PATENT NO. : 6,159,010
DATED : December 12, 2000
INVENTOR(S) : Rogers et al.

Page 1 of 1

It is certified that error appears in the above-identified patent and that said Letters Patent is hereby corrected as shown below:

Column 4, claim 10,
Line 13, delete "though" and insert -- through --

Claim 11,
Line 17, after "to" insert -- be --

Claim 14,
Line 32, after "in" insert -- a --

Claim 18,
Line 45, after "with" delete "an" and insert -- a --

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*